United States Patent [19]

Akamine

[11] Patent Number: 4,851,351
[45] Date of Patent: Jul. 25, 1989

[54] CULTURE VESSEL

[75] Inventor: Akinori Akamine, Yokohama, Japan

[73] Assignee: Sumitomo Bakelite Company Limited, Tokyo, Japan

[21] Appl. No.: 147,514

[22] Filed: Jan. 25, 1988

[51] Int. Cl.$^4$ ............................................. C12M 1/24
[52] U.S. Cl. .................................. 435/296; 435/284; 435/299; 220/DIG. 14; 215/31; 215/10
[58] Field of Search .................... 215/10, 31; 222/572; 435/284, 285, 286, 296, 299; 220/DIG. 12, DIG. 13, DIG. 14

[56] References Cited

U.S. PATENT DOCUMENTS 4,334,028  6/1982  Carver ................................ 435/284

FOREIGN PATENT DOCUMENTS 2185997  8/1987  United Kingdom ................ 435/296

Primary Examiner—Albert J. Makay
Assistant Examiner—Noah Kamen
Attorney, Agent, or Firm—Stevens, Davis, Miller & Mosher

[57] ABSTRACT

A culture vessel used for microorganism culture, cell culture, tissue culture and the like, which has features with regard to a shape of the opening neck for enabling to perform various operations such as introduction of a culture area solution and insertion of pipettes or the like. In the conventional culture vessel, the opening parts at the opening end of the neck and the connecting part joining the vessel body with the neck have been of circular shapes and they have diameters of equal dimension to provide a straight pipe configuration for the opening neck. This gives rise to the problems that a dead angle is formed for a culture area during operation. In the culture vessel according to the invention, the shape of inner peripheral wall of the opening end of the opening neck diameter of the inner peripheral wall of the connecting part is substantially the same as the diameter of the inner peripheral wall of the opening end, and a minimum diameter of the inner peripheral wall of the connecting part is 20 to 90% of the maximum diameter, whereby the abovementioned problems are solved.

1 Claim, 3 Drawing Sheets 4,851,351

CULTURE VESSEL

BACKGROUND OF THE INVENTION

1. Field of the Invention

The present invention generally relates to a culture vessel which is used for microorganism culture, cell culture, tissue culture and the like and, more particularly, to the structure of the neck constituting its opening part.

2. Description of the Prior Art

Conventionally, in the culture vessel with a cap on the neck, it is commonly known that the opening parts are round or of circular cross-section at the opening end A of the neck C and at the connecting part B joining the body D with the neck C respectively, and these opening parts have almost the same inner diameters, as illustrated in FIGS. 5, 6A and 6B (For example, U.S. Pat. No. Des. 285725). This form of the neck which has a straight pipe-shaped opening part has been used since early times, no matter whether the flask was made of glass or of synthetic resins. However, the limit of the opening areas of the opening end A and the connecting part B has caused the inconveniences enumerated hereinafter. That is to say, when an attempt to enlarge the respective opening areas at the opening end A and the connecting part B is made, the height of the entire culture vessel is increased making the form of the vessel unstable, and this gives rise to the defect that the vessels can not be stacked one on top of another, although such operations as introducing culture solution, inserting the pipette or the like may be easily practiced. On the other hand, when an attempt is made to decrease the diameter of the opening end A and the connecting part B respectively or to increase the length of the neck C with a view to making the form of the vessel stable and to facilitating piling up of the vessels, it becomes very inconvenient to perform the abovementioned operations and this gives rise to the defect that a dead angle appears during reagent sprinkling to the culture area or sucking of the cells from the culture area.

The above-mentioned defects are caused no matter whether the culture vessel is made of glass or of synthetic resins, and up to the present there have been no culture vessels having the form and structure which are evaluated as the most suitable ones.

SUMMARY OF THE INVENTION

An object of the present invention is to provide a culture vessel which obviates the above-mentioned defects, facilitates to perform such manual operations as introducing a culture solution and inserting pipettes for the purpose of gathering samples without difficulty, and has stable form and structure making easy to stack a plurality of the vessels one on another.

According to the invention, there is provided a culture vessel comprising a vessel body, an opening neck provided on one side of the vessel body and having an opening end to which a cap is fitted, the opening end having n inner peripheral wall of circular shape, and a connecting part joining the vessel body with the opening neck and having an inner peripheral wall which constitutes an opening part of the vessel body to the opening neck, the maximum inside dimension of the inner peripheral wall of the connecting part is substantially equal to the diameter of the inner peripheral wall of the opening end and the minimum inside dimension of the inner peripheral wall of the connecting part is 20 to 90% of the maximum inside dimension.

The culture vessel according to the invention may be constituted as a culture bottle, a culture flask, a culture roller bottle or the like. No matter whether the culture vessel is made of glass or of synthetic resins, the invention is applicable thereto. However, since the necks of the culture vessels have to be manufactured precisely, it is preferable that both the cap and the vessel body are made of synthetic resins.

DETAILED DESCRIPTION OF THE PREFERRED EMBODIMENT

A culture vessel according to an embodiment of the invention will be described hereunder with reference to the drawings.

Figure 1A:
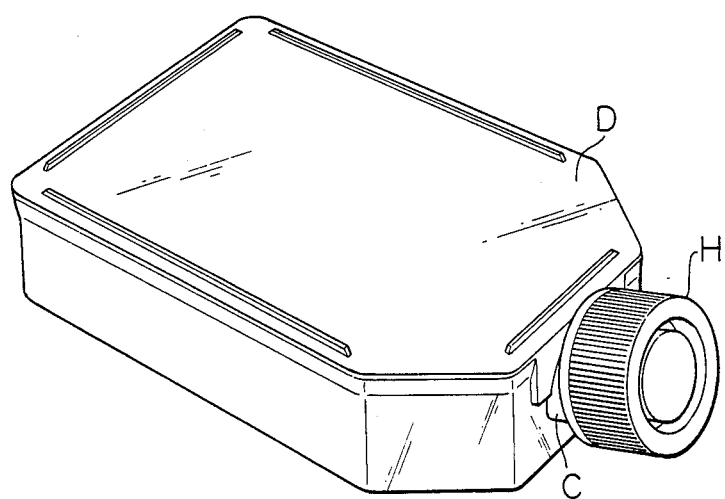
FIG. 1A is a perspective view showing a culture vessel according to an embodiment of the invention.
Figure 1B:
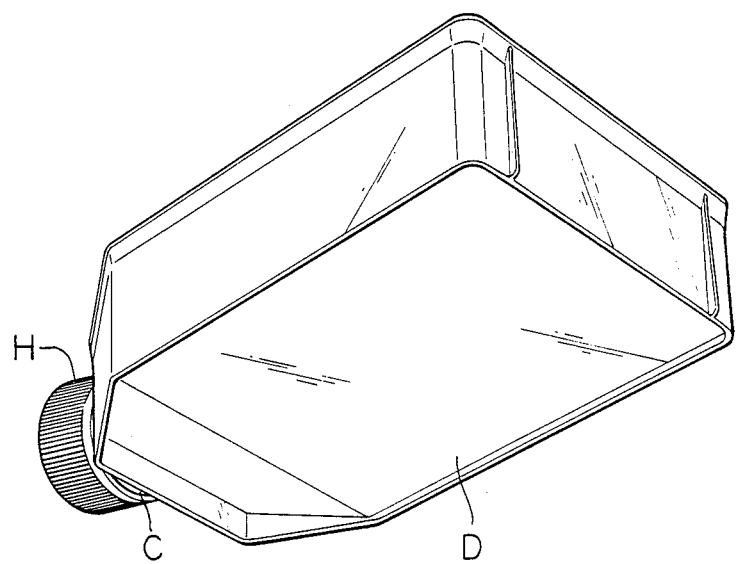
FIG. 1B is a perspective view showing the culture vessel in a state seen from a direction different from the case of FIG. 1A.
Figure 1C:
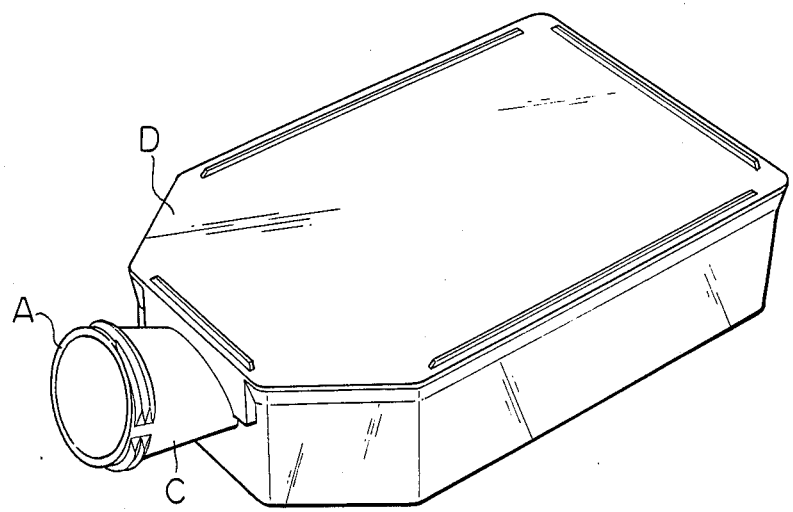
FIG. 1C is a perspective view showing the culture vessel in a state seen from a direction different from the cases of FIGS. 1A and 1B and having a cap removed from a vessel body.
Figure 1D:
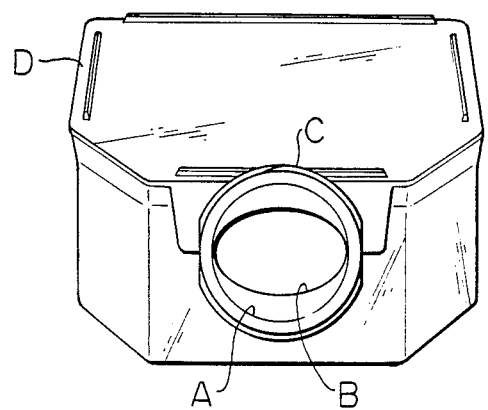
FIG. 1D is a perspective view showing the culture vessel in a state seen from the vessel body.
Figure 2:
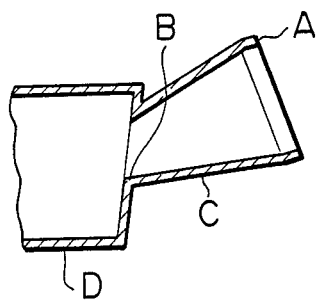
FIG. 2 is a cross-sectional view showing the structure or shape of an opening neck of the culture vessel.
Figure 3A:
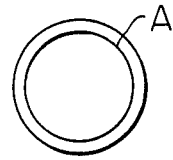
FIGS. 3A and 3B show configurations of an opening end of the neck and a connecting part joining the vessel body with the neck, respectively.

As shown in FIGS. 1A to 1D, 2, 3A and 3B, the culture vessel includes a vessel body D, and an opening neck C. The neck C constituting an opening part for the culture vessel is provided on one side of the vessel body D and having an opening end A. The opening end A, to which a cap H is fitted, has an inner peripheral wall of circular shape as best shown in FIG. 3A. The vessel body D is joined with the neck C through a connecting part B.

Figure 3B:
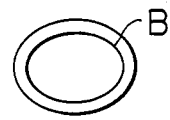
Figure 4A:
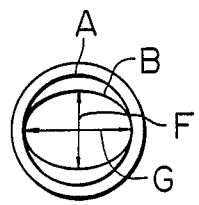
FIGS. 4A and 4B are views explaining forms or shapes of inner peripheral walls of the opening end of the neck and the connecting part, respectively.
Figure 4B:
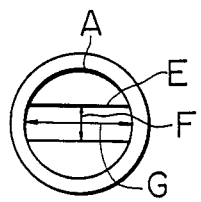
Figure 5:
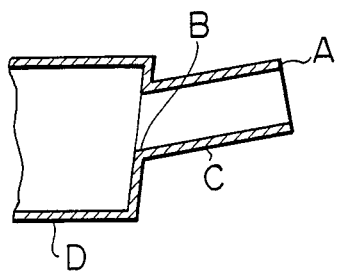
FIG. 5 is a cross-sectional view showing the structure or shape of a neck of the conventional culture vessel.
Figure 6A:
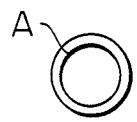
FIGS. 6A and 6B show the configurations of an opening end of the neck and a connecting part joining a vessel body with the neck, respectively, of the culture vessel shown in FIG. 5.
Figure 6B:
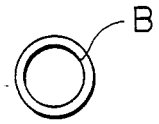

The inner peripheral wall of the connecting part B, which constitutes an opening part of the vessel body D to the neck C, has such a shape that the inside dimension or diameter measured in an upward and downward direction or a vertical direction as viewed in FIG. 3B is smaller than the inside dimension or diameter measured in a leftward and rightward direction or a horizontal direction as viewed in FIG. 3B. Thus, the shape or circumferential contour of the inner peripheral wall of the connecting part B is substantially oval as shown in FIG. 3B. As the shape of this inner peripheral wall, an ellipse, a rectangle having both longitudinal sides shaped arcuate as shown in FIG. 4B, or the like may be adopted in addition to the oval as shown in FIG. 3B. Is not limited to the oval as shown in FIG. 3B, though the shape of the inner peripheral wall is not limited to these forms. As shown in FIGS. 4A and 4B, a maximum inside dimention or diameter G of the connecting parts B and E is substantially equal to the inner diameter of the opening end A of the neck C, whereas a minimum inside dimension or diameter F thereof is suitably determined to 20 to 90 percent (%), more preferably 30 to 70 percent (%), of the maximum diameter G. In the case where the ratio of the minimum inside dimension or diameter to the maximum inside dimension or diameter of the connecting part B is less than 20 percent, the minimum diameter of the inner peripheral wall of the connecting part becomes too small and, therefore, it is almost impossible to introduce a culture are solution and to insert the pipette through the opening part into the culture vessel. On the other hand, if the ratio in question is greater than 90 percent, the culture vessel suffers from the previously described problems in the conventional culture vessels in that a dead angle is liable to appear in the culture area and the opening part tends to be small when the pipette is inserted. An important feature of the invention resides in that the opening area at the opening end A is made to become still larger than the maximum sectional area which can be taken as the area of the opening part at the connecting part B, and hence freedom in performing the pipette operation is enhanced and the pipette operation is facilitated.

According to the present invention, it is possible to make the dimension or diameter of the opening end of the neck larger than the dimension of the side of the vessel; i.e., larger than the dimension or diameter of the opening neck of the convention culture vessel. Thus, the disadvantages of the conventional vessel can be fully removed. Namely, since the pipette may be readily inserted into the culture vessel and it may be moved or operated within a wide range in forward and rearward, and upward and downward directions, a dead angle for the pipette with respect to the culture vessel is not formed and it is possible to make the sample cells remained in very small quantity after performing the operation of removing the cells from the vessel. Further, since it is unnecessary to increase the height of the vessel, the vessel having a stable form which may be easily stacked one on another may be advantageously obtained.

What is claimed is:

1. A culture vessel, comprising:
a vessel body;
an opening neck provided on one side of said vessel body, said opening neck being hollow and having an opening end adapted to receive a cap thereon, said opening end having a circular shaped inner peripheral wall to define a circular opening; and
a connecting part joining said vessel body and said opening neck, said connecting part comprising an inner peripheral wall defining an opening to provide communication between an interior of said vessel body and said opening neck, said opening of said connecting part being in the shape of one of an oval, ellipse, and a four-sided figure having two opposite arcuate-shape longitudinal sides;
a maximum dimension of said opening of said connecting part being substantially equal to the diameter of said circular opening of said opening end; and
a minimum dimension of said opening of said connecting part being 30–70% of said maximum dimension.

* * * * *